(12) United States Patent
Rezayi

(10) Patent No.: US 11,882,982 B2
(45) Date of Patent: Jan. 30, 2024

(54) SHOE SANITIZING ASSEMBLY

(71) Applicant: Hakimeh Rezayi, Anaheim, CA (US)

(72) Inventor: Hakimeh Rezayi, Anaheim, CA (US)

( * ) Notice: Subject to any disclaimer, the term of this patent is extended or adjusted under 35 U.S.C. 154(b) by 457 days.

(21) Appl. No.: 17/204,630

(22) Filed: Mar. 17, 2021

(65) Prior Publication Data

US 2022/0296076 A1 Sep. 22, 2022

(51) Int. Cl.
*A47L 23/02* (2006.01)
*A47L 23/26* (2006.01)
*A61L 2/18* (2006.01)
*A61L 2/26* (2006.01)

(52) U.S. Cl.
CPC .............. *A47L 23/266* (2013.01); *A47L 23/02* (2013.01); *A47L 23/263* (2013.01); *A61L 2/18* (2013.01); *A61L 2/26* (2013.01); *A61L 2202/14* (2013.01); *A61L 2202/15* (2013.01)

(58) Field of Classification Search
None
See application file for complete search history.

(56) References Cited

U.S. PATENT DOCUMENTS

| 6,668,842 B1 | 12/2003 | Wilke |
| D599,957 S | 9/2009 | Reggaro |
| 8,533,888 B2 | 9/2013 | Kessler |
| 9,049,978 B1 | 6/2015 | Shamberger |
| 10,426,316 B2 | 10/2019 | Gold |
| 2007/0271715 A1 | 11/2007 | Scoralle |

FOREIGN PATENT DOCUMENTS

WO    WO2004045362    6/2004

*Primary Examiner* — Levon J Shahinian

(57) ABSTRACT

A shoe sanitizing assembly includes a pan that is positionable adjacent to an entry of a building such that the pan can to be stepped in by patrons of the building. A plurality of biasing members is each coupled to and extends upwardly from the pan. A mat is positionable on top of the plurality of biasing members such that the patrons of the building step on the mat when the patrons pass through the entry. A pair of fluid reservoirs is provided that each contains a fluid and each of the fluid reservoirs is positioned in the pan. A plurality of pumps is each positioned in the pan. Each of the pumps is actuated when the mat is stepped upon to spray a measured amount of the fluid outwardly through the mat onto soles of shoes worn by the user.

6 Claims, 5 Drawing Sheets

SHOE SANITIZING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to sanitizing devices and more particularly pertains to a new sanitizing device for sanitizing soles of shoes. The device includes a pan and a mat that is positioned in the pan. A plurality of pumps is positioned in the pan which spray a sanitizer when the mat is stepped on for sanitizing soles of shoes.

(2) Description of Related Art Including Information Disclosed Under 37 CFR 1.97 and 1.98

The prior art relates to sanitizing devices including a variety of shoe cleaning devices that include various means of frictionally cleaning soles of shoes when the sanitizing device is stepped upon. Additionally, the prior art discloses a variety of shoe sanitizing devices that include an absorbent surface that is infused with a fluid disinfectant upon which a user can step to sanitize soles of the user's shoes.

BRIEF SUMMARY OF THE INVENTION

An embodiment of the disclosure meets the needs presented above by generally comprising a pan that is positionable adjacent to an entry of a building such that the pan can to be stepped in by patrons of the building. A plurality of biasing members is each coupled to and extends upwardly from the pan. A mat is positionable on top of the plurality of biasing members such that the patrons of the building step on the mat when the patrons pass through the entry. A pair of fluid reservoirs is provided that each contains a fluid and each of the fluid reservoirs is positioned in the pan. A plurality of pumps is each positioned in the pan. Each of the pumps is actuated when the mat is stepped upon to spray a measured amount of the fluid outwardly through the mat onto soles of shoes worn by the user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
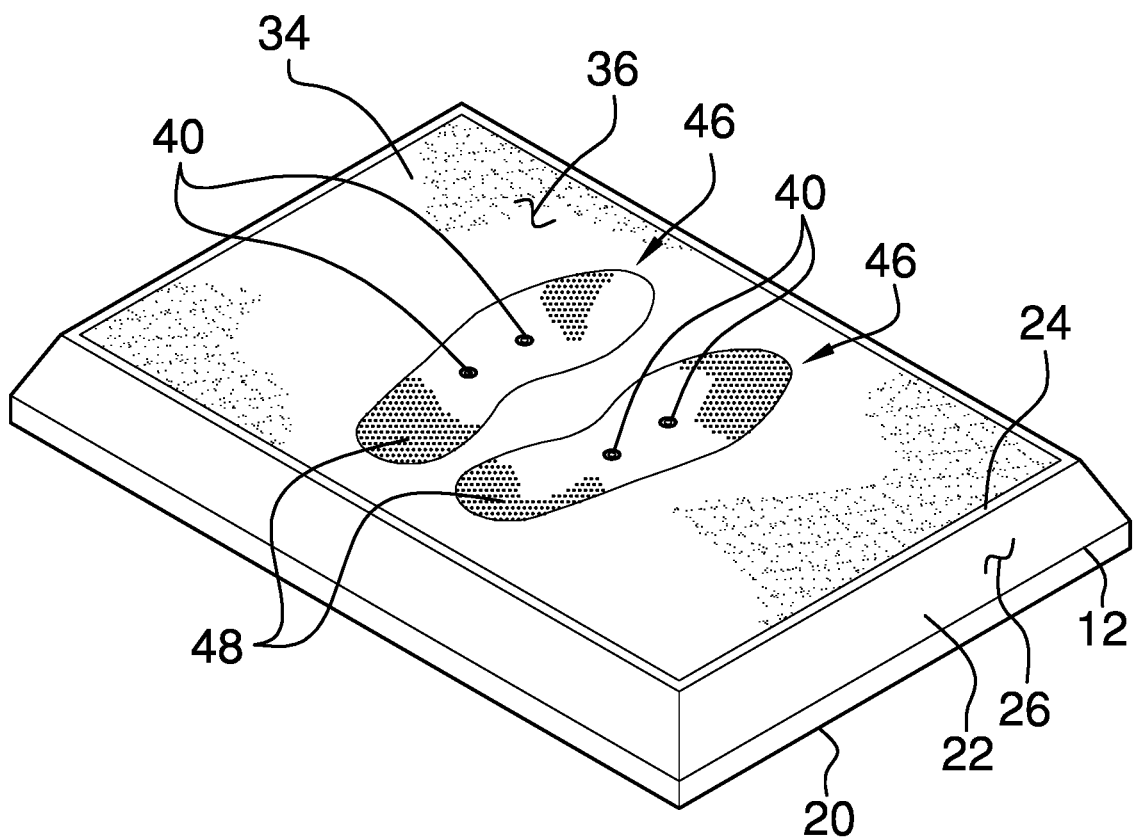
FIG. 1 is a top perspective view of a shoe sanitizing assembly according to an embodiment of the disclosure.
Figure 2:
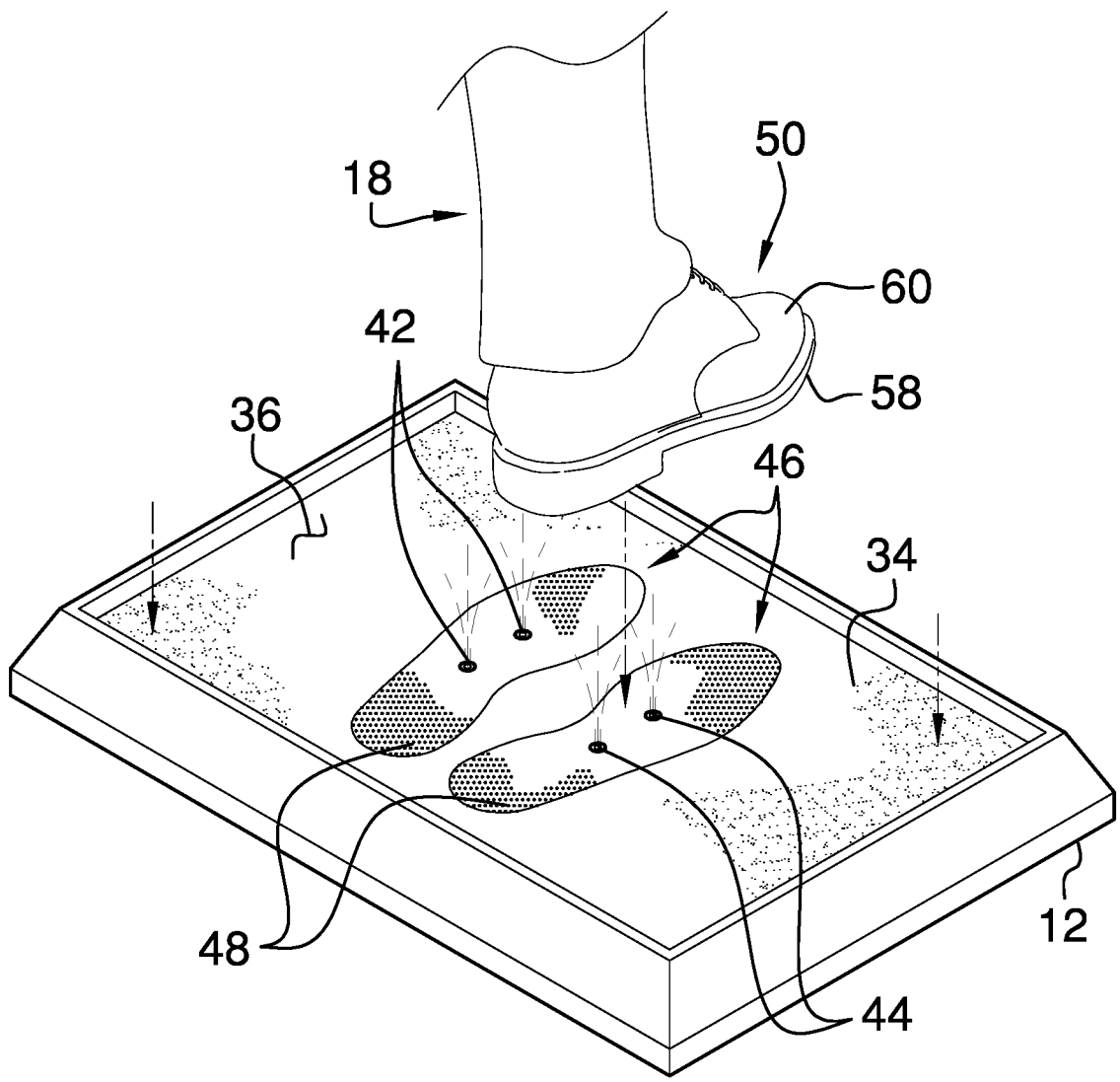
FIG. 2 is a top perspective in-use view of an embodiment of the disclosure.
Figure 3:
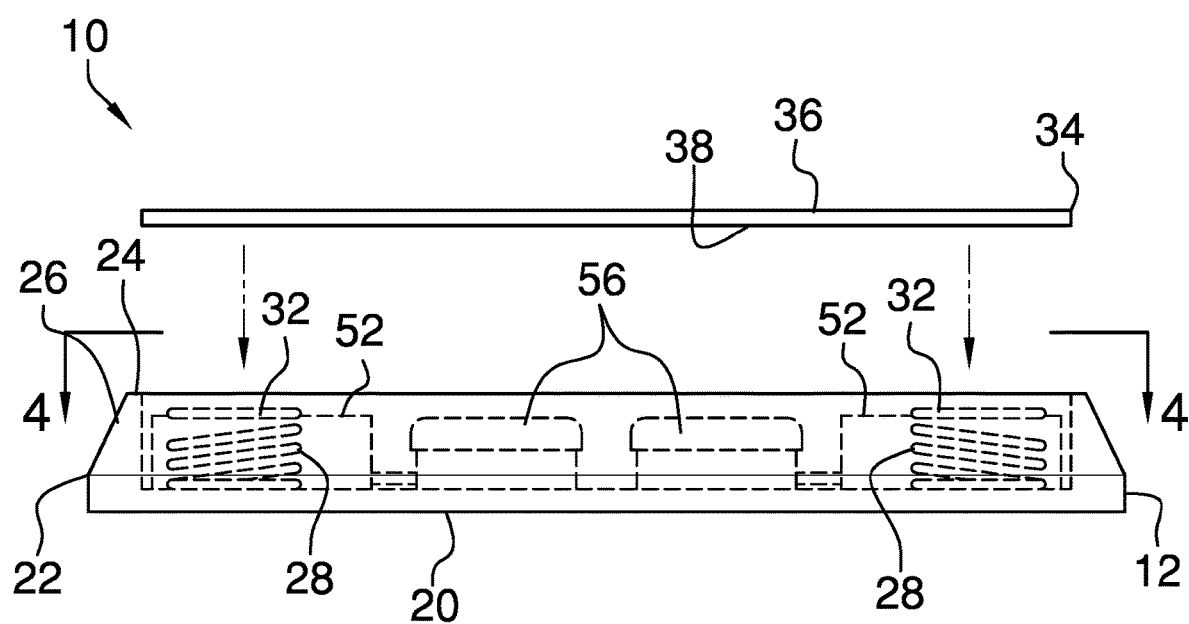
FIG. 3 is a front phantom view of an embodiment of the disclosure.
Figure 4:
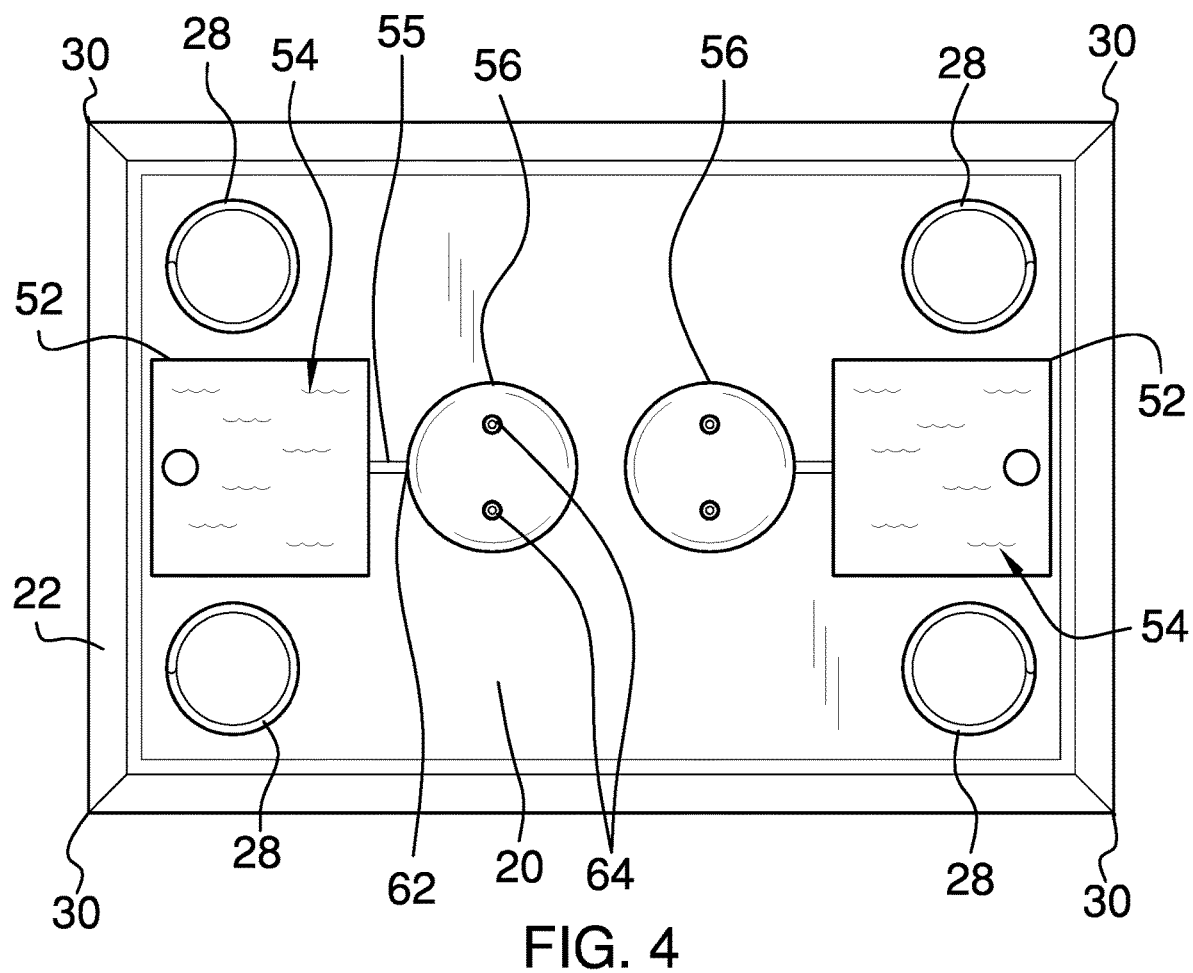
FIG. 4 is a cross sectional view taken along line 4-4 of FIG. 3 of an embodiment of the disclosure.
Figure 5:
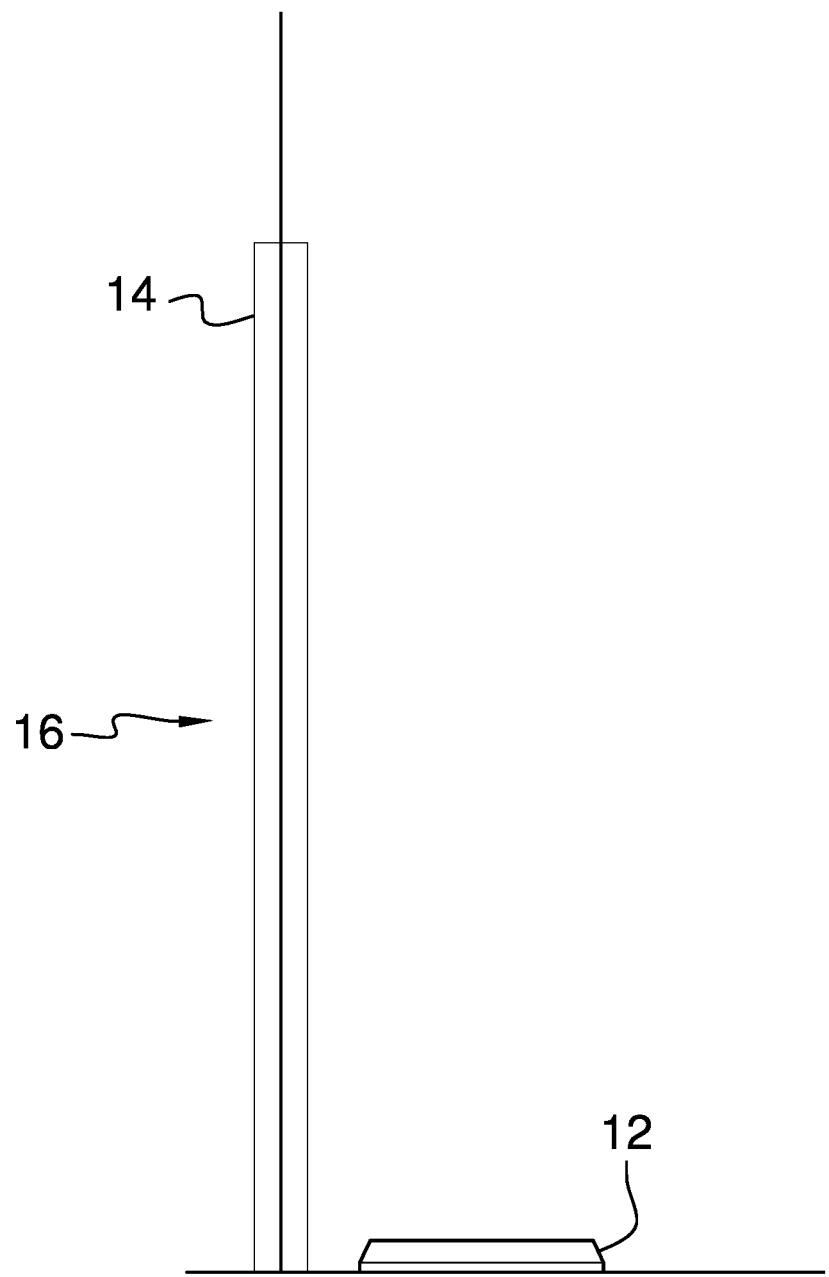
FIG. 5 is a perspective in-use view of an embodiment of the disclosure.

With reference now to the drawings, and in particular to FIGS. 1 through 5 thereof, a new sanitizing device embodying the principles and concepts of an embodiment of the disclosure and generally designated by the reference numeral 10 will be described.

As best illustrated in FIGS. 1 through 5, the shoe sanitizing assembly 10 generally comprises a pan 12 that is positionable adjacent to an entry 14 of a building 16. In this way patrons 18 of the building 16 can step in the pan 12 when the patrons 18 pass through the entry 14. The pan 12 has a bottom wall 20 and a perimeter wall 22 extending upwardly therefrom, and the perimeter wall 22 has a distal edge 24 with respect to the bottom wall 20 and an outwardly facing surface 26 extending between the distal edge 24 and the bottom wall 20. The outwardly facing surface 26 is sloped at an angle between the bottom wall 20 and the distal edge 24. The building 16 may be a public building, such as a hospital or school, or the building 16 may be a private residence.

A plurality of biasing members 28 is each coupled to and extends upwardly from the pan 12 and each of the biasing members 28 is positioned on the bottom wall 20. Each of the biasing members 28 is aligned with a respective one of four corners 30 of the pan 12 and each of the biasing members 28 has a distal end 32 with respect to the bottom wall 20. Each of the biasing members 28 is resiliently compressible between the distal end 32 and the bottom wall 20. Additionally, the distal end 32 of each of the biasing members 28 is positioned below the distal edge 24 of the perimeter wall 22 of the pan 12. Each of the biasing members 28 may comprise a spring, a gas charged piston or other type of resiliently compressible biasing member.

A mat 34 is provided and the mat 34 is positionable on top of the plurality of biasing members 28. Thus, the patrons 18 of the building 16 step on the mat 34 when the patrons 18 pass through the entry 14. Additionally, the biasing members 28 are compressed when a patron 18 steps on the mat 34. The mat 34 has a top surface 36 and a bottom surface 38, and the bottom surface 38 rests on the distal end 32 of each of the biasing members 28 such that the top surface 36 is aligned with the distal edge 24 of the perimeter wall 22 of the pan 12.

The mat 34 has a plurality of openings 40 each extending through the top surface 36 and the bottom surface 38. The plurality of openings 40 includes a set of first openings 42 and a set of second openings 44. Additionally, indicia 46 are printed on the top surface 36 and the indicia 46 comprise a pair of footprints 48 to visually communicate where the patron 18 should place their feet 50. Each of the first openings 42 and the second openings 44 is positioned in a respective one of the footprints 48.

A pair of fluid reservoirs 52 is provided and each of the reservoirs 52 contains a fluid 54. The fluid 54 may be a chemical sanitizer that is approved for human use. Each of the fluid reservoirs 52 is positioned in the pan 12 and each of the fluid reservoirs 52 has an outlet 55. A plurality of pumps 56 is each positioned in the pan 12 and each of the pumps 56 is in fluid communication with a respective one of the reservoirs 52. In this way each of the pumps 56 can receive the fluid 54 in the respective fluid reservoir 52. Each of the pumps 56 is actuated when the mat 34 compresses the biasing members 28 and each of the pumps 56 sprays a measured amount of the fluid 54 outwardly through the mat 34 when the pumps 56 are actuated. In this way each of the pumps 56 can deliver the fluid 54 onto soles 58 of shoes 60 being worn by the patron 18.

Each of the pumps 56 has an input 62 and a plurality of outputs 64, and the input 62 of each of the pumps 56 is fluidly coupled to the outlet 55 of the respective reservoir. Each of the outputs 64 on each of the pumps 56 is aligned with respective ones of the first openings 42 and the second openings 44 in the mat 34. In this way each of the outputs 64 can direct the fluid 54 outwardly through the respective first opening 42 and second opening 44 when the pumps 56 are actuated. Each of the pumps 56 may comprise a manually operated, compressible pump that is actuated when the pumps 56 are compressed as a result of the patron 18 stepping on the mat 34.

In use, the pan 12 is positioned adjacent to the entry 14 to the building 16 such that the patrons 18 of the building 16 step on the mat 34 as the patrons 18 pass through the entry 14. The patrons 18 step on each of the footprints 48 on the mat 34 and the mat 34 compresses the biasing members 28 and each of the pumps 56. Thus, each of the pumps 56 sprays the fluid 54 outwardly through each of the openings 40 in the mat 34 to sanitize the soles 58 of the patron's shoes 60. In this way the patron 18 is inhibited from tracking in bacteria and other contaminants when the patron 18 enters the building 16.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A shoe sanitizing assembly for sanitizing a sole of a shoe, said assembly comprising:
   a pan being positionable adjacent to an entry of a building wherein said pan is configured to be stepped in by patrons of the building;
   a plurality of biasing members, each of said biasing members being coupled to and extending upwardly from said pan;
   a mat being positionable on top of said plurality of biasing members wherein said mat is configured to be stepped on by the patrons of the building when the patrons pass through the entry, said biasing members being compressed when a patron steps on said mat;
   a pair of fluid reservoirs each being configured to contain a fluid, each of said fluid reservoirs being positioned in said pan;
   a plurality of pumps, each of said pumps being positioned in said pan, each of said pumps being in fluid communication with a respective one of said reservoirs wherein each of said pumps is configured to receive the fluid in said respective reservoir, each of said pumps being actuated when said mat compresses said biasing members, each of said pumps spraying a measured amount of the fluid outwardly through said mat when said pumps are actuated wherein each of said pumps is configured to deliver the fluid onto soles of shoes being worn by the user;
   wherein said pan has a bottom wall and a perimeter wall extending upwardly therefrom, said perimeter wall having a distal edge with respect to said bottom wall and an outwardly facing surface extending between said distal edge and said bottom wall, said outwardly facing surface being sloped at an angle between said bottom wall and said distal edge; and
   wherein each of said biasing members is positioned on said bottom wall, each of said biasing members being aligned with a respective one of four corners of said pan, each of said biasing members having a distal end with respect to said bottom wall, each of said biasing members being resiliently compressible between said distal end and said bottom wall, said distal end of each of said biasing members being positioned below said distal edge of said perimeter wall of said pan.

2. The assembly according to claim 1, wherein said mat has a top surface and a bottom surface, said bottom surface resting on said distal end of each of said biasing members such that said top surface is aligned with said distal edge of said perimeter wall of said pan.

3. The assembly according to claim 2, wherein said mat has a plurality of openings each extending through said top surface and said bottom surface, said plurality of openings including a set, of first openings and a set, of second openings.

4. The assembly according to claim 3, wherein said top surface has indicia being printed thereon, said indicia comprising a pair of footprints wherein said indicia is configured to visually communicate where the user should place their feet, each of said first openings and said second openings being positioned in a respective one of said footprints.

5. The assembly according to claim 3, wherein:
each of said fluid reservoirs has an outlet; and
each of said pumps has an input and a plurality of outputs, said input of each of said pumps being fluidly coupled to said outlet of said respective reservoir, each of said outputs on each of said pumps being aligned with respective ones of said first openings and said second openings in said mat wherein each of said outputs is configured to direct, the fluid outwardly through said respective first opening and second opening when said pumps are actuated.

6. A shoe sanitizing assembly for sanitizing a sole of a shoe, said assembly comprising:
a pan being positionable adjacent to an entry of a building wherein said pan is configured to be stepped in by patrons of the building, said pan having a bottom wall and a perimeter wall extending upwardly therefrom, said perimeter wall having a distal edge with respect to said bottom wall and an outwardly facing surface extending between said distal edge and said bottom wall, said outwardly facing surface being sloped at an angle between said bottom wall and said distal edge;
a plurality of biasing members, each of said biasing members being coupled to and extending upwardly from said pan, each of said biasing members being positioned on said bottom wall, each of said biasing members being aligned with a respective one of four corners of said pan, each of said biasing members having a distal end with respect to said bottom wall, each of said biasing members being resiliently compressible between said distal end and said bottom wall, said distal end of each of said biasing members being positioned below said distal edge of said perimeter wall of said pan;
a mat being positionable on top of said plurality of biasing members wherein said mat is configured to be stepped on by the patrons of the building when the patrons pass through the entry, said biasing members being compressed when a patron steps on said mat, said mat having a top surface and a bottom surface, said bottom surface resting on said distal end of each of said biasing members such that said top surface is aligned with said distal edge of said perimeter wall of said pan, said mat having a plurality of openings each extending through said top surface and said bottom surface, said plurality of openings including a set of first openings and a set of second openings, said top surface having indicia being printed thereon, said indicia comprising a pair of footprints wherein said indicia is configured to visually communicate where the user should place their feet, each of said first openings and said second openings being positioned in a respective one of said footprints;
a pair of fluid reservoirs each being configured to contain a fluid, each of said fluid reservoirs being positioned in said pan, each of said fluid reservoirs having an outlet;
a plurality of pumps, each of said pumps being positioned in said pan, each of said pumps being in fluid communication with a respective one of said reservoirs wherein each of said pumps is configured to receive the fluid in said respective reservoir, each of said pumps being actuated when said mat compresses said biasing members, each of said pumps spraying a measured amount of the fluid outwardly through said mat when said pumps are actuated wherein each of said pumps is configured to deliver the fluid onto soles of shoes being worn by the user, each of said pumps having an input and a plurality of outputs, said input of each of said pumps being fluidly coupled to said outlet of said respective reservoir, each of said outputs on each of said pumps being aligned with respective ones of said first openings and said second openings in said mat wherein each of said outputs is configured to direct the fluid outwardly through said respective first opening and second opening when said pumps are actuated.

\* \* \* \* \*